(12) United States Patent
Dickhans et al.

(10) Patent No.: US 11,147,621 B2
(45) Date of Patent: Oct. 19, 2021

(54) SYSTEMS AND METHODS FOR ABLATING TISSUE

(71) Applicant: COVIDIEN LP, Mansfield, MA (US)

(72) Inventors: William J. Dickhans, Longmont, CO (US); Flor De Maria R. Nonalaya, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 470 days.

(21) Appl. No.: 16/158,733

(22) Filed: Oct. 12, 2018

(65) Prior Publication Data

US 2019/0125444 A1 May 2, 2019

Related U.S. Application Data

(60) Provisional application No. 62/580,838, filed on Nov. 2, 2017.

(51) Int. Cl.
*A61B 18/18* (2006.01)
*A61B 18/14* (2006.01)
(Continued)

(52) U.S. Cl.
CPC ...... *A61B 18/1815* (2013.01); *A61B 18/1492* (2013.01); *A61B 2018/00011* (2013.01);
(Continued)

(58) Field of Classification Search
CPC ............ A61B 18/1492; A61B 18/1815; A61B 2018/00011; A61B 2018/00023;
(Continued)

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CN | 1103807 A | 6/1995 |
| DE | 390937 C | 3/1924 |

(Continued)

OTHER PUBLICATIONS

European Search Report dated Mar. 20, 2019, corresponding to counterpart European Application No. 18 20 3924.8; 7 pages.

(Continued)

*Primary Examiner* — Daniel W Fowler
(74) *Attorney, Agent, or Firm* — Carter, DeLuca & Farrell LLP

(57) ABSTRACT

A microwave ablation system includes a microwave ablation antenna assembly, a generator, a first fluid supply source, and a second fluid supply source. The microwave ablation antenna assembly includes a fluid port for receiving fluid. The generator is coupled to the microwave ablation antenna assembly. The first fluid supply source is configured to be selectively in fluid communication with the fluid port to supply a first fluid to the microwave ablation antenna assembly. The second fluid supply source is configured to be selectively in fluid communication with the fluid port to supply a second fluid to the microwave ablation antenna assembly.

18 Claims, 7 Drawing Sheets

(51) Int. Cl.
    *A61B 18/00* (2006.01)
    *A61M 25/00* (2006.01)
(52) U.S. Cl.
    CPC .............. *A61B 2018/00023* (2013.01); *A61B 2018/00577* (2013.01); *A61B 2018/00702* (2013.01); *A61B 2018/00791* (2013.01); *A61B 2018/00898* (2013.01); *A61B 2018/1823* (2013.01); *A61B 2018/1838* (2013.01); *A61B 2018/1846* (2013.01); *A61B 2018/1853* (2013.01); *A61M 25/00* (2013.01)
(58) Field of Classification Search
    CPC ........... A61B 2018/00577; A61B 2018/00702; A61B 2018/00791; A61B 2018/00898; A61B 2018/1823; A61B 2018/1838; A61B 2018/1846
    See application file for complete search history.

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| 4,781,175 A * | 11/1988 | McGreevy | A61B 18/042 219/121.5 |
| D354,218 S | 1/1995 | Van de Peer | |
| D424,693 S | 5/2000 | Pruter | |
| D424,694 S | 5/2000 | Tetzlaff et al. | |
| D425,201 S | 5/2000 | Tetzlaff et al. | |
| 6,097,985 A * | 8/2000 | Kasevich | A61B 18/18 607/100 |
| D449,886 S | 10/2001 | Tetzlaff et al. | |
| D457,958 S | 5/2002 | Dycus et al. | |
| D457,959 S | 5/2002 | Tetzlaff et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| D564,662 S | 3/2008 | Moses et al. | |
| D576,932 S | 9/2008 | Strehler | |
| 7,465,300 B2 | 12/2008 | Arless et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| D681,810 S | 5/2013 | DeCarlo | |
| 9,186,197 B2 | 11/2015 | McKay | |
| 9,379,444 B2 | 6/2016 | Bonn | |
| 9,480,527 B2 | 11/2016 | Prakash et al. | |
| 9,498,285 B2 | 11/2016 | Behnke | |
| 9,526,557 B2 | 12/2016 | Brannan | |
| 9,526,568 B2 | 12/2016 | Ohri et al. | |
| 9,526,575 B2 | 12/2016 | Prakash et al. | |
| 9,549,778 B2 | 1/2017 | Shiu et al. | |
| 9,717,551 B2 | 8/2017 | Krueger et al. | |
| 9,814,844 B2 | 11/2017 | Ohri et al. | |
| 9,820,813 B2 | 11/2017 | Brannan | |
| 2003/0236487 A1* | 12/2003 | Knowlton | A61B 18/1402 604/20 |
| 2011/0208179 A1* | 8/2011 | Prakash | A61B 18/1477 606/33 |
| 2013/0289678 A1 | 10/2013 | Clark et al. | |
| 2014/0276200 A1* | 9/2014 | Brannan | A61B 18/1815 600/562 |
| 2015/0105659 A1 | 4/2015 | Salahieh et al. | |
| 2015/0320478 A1 | 11/2015 | Cosman, Jr. et al. | |
| 2016/0354144 A1 | 12/2016 | Caplan et al. | |
| 2017/0007310 A1 | 1/2017 | Rajagopalan et al. | |
| 2017/0007324 A1 | 1/2017 | Kadamus et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 3/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1159926 A2 | 3/2003 |
| FR | 179 607 | 11/1906 |
| FR | 1275415 A | 11/1961 |
| FR | 1347865 A | 1/1964 |
| FR | 2 235 669 A1 | 1/1975 |
| FR | 2 276 027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2 862 813 A1 | 5/2005 |
| FR | 2 864 439 A1 | 7/2005 |
| JP | 56161636 | 12/1981 |
| JP | 5958933 | 4/1984 |
| JP | 55106 | 1/1993 |
| JP | 508933 | 2/1993 |
| JP | H0540112 A | 2/1993 |
| JP | H06343644 A | 12/1994 |
| JP | H07265328 A | 10/1995 |
| JP | 08056955 | 3/1996 |
| JP | 08252263 A | 10/1996 |
| JP | 09000492 A | 1/1997 |

(56) References Cited

FOREIGN PATENT DOCUMENTS

| | | |
|---|---|---|
| JP | H0910223 A | 1/1997 |
| JP | 9117456 | 5/1997 |
| JP | H11244298 A | 9/1999 |
| JP | 2000342599 A | 12/2000 |
| JP | 2000350732 A | 12/2000 |
| JP | 2001003776 A | 1/2001 |
| JP | 2001008944 | 1/2001 |
| JP | 2001029356 | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 0036985 A2 | 6/2000 |
| WO | 2010035831 A1 | 4/2010 |

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.™. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.™. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.™. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. Ml, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140(Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).

(56) References Cited

OTHER PUBLICATIONS

Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al. , "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology (Date Unknown). "Overcoming the Challenge" located at: <http://www.urologix.com/medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.

\* cited by examiner

SYSTEMS AND METHODS FOR ABLATING TISSUE

CROSS-REFERENCE TO RELATED APPLICATION

This application claims the benefit of and priority to U.S. Provisional Application No. 62/580,838, filed Nov. 2, 2017, the entire contents of which being incorporated by reference herein.

BACKGROUND

1. Technical Field

The present disclosure relates to microwave surgical devices suitable for use in tissue ablation applications.

2. Discussion of Related Art

Treatment of certain diseases requires the destruction of malignant tissue growths, e.g., tumors. In this regard, electrosurgical devices utilizing electromagnetic radiation have been developed to heat and destroy tumor cells. For example, apparatus for use in ablation procedures include a power generation source, e.g., a microwave or radio frequency (RF) electrosurgical generator that functions as an energy source, and a surgical instrument (e.g., ablation probe having an antenna assembly) for directing energy to the target tissue. A cable assembly having a plurality of conductors operatively couple and transmit energy from the generator to the instrument. The cable assembly also communicates control, feedback and identification signals between the instrument and the generator.

During treatment, the ablation probe may be inserted into tissues where cancerous tumors have been identified. Once the probe is positioned, electrosurgical energy is passed through the probe and into surrounding tissue to form an "ablation zone." The energy applied to the tissue denatures the cancerous cells at elevated temperatures that are slightly lower than temperatures normally injurious to healthy cells. To perform the ablative procedure with more specificity and accuracy, the ablation zone in which ablative energy is output may be more precisely controlled, which may provide improved results. In this regard, there is a need for improved control of the ablation zone.

SUMMARY

According to an aspect of the present disclosure, a microwave ablation system is provided. The microwave ablation system includes a microwave ablation antenna assembly, a generator, a first fluid supply source, and a second fluid supply source. The microwave ablation antenna assembly includes a fluid port for receiving fluid. The generator is coupled to the microwave ablation antenna assembly. The first fluid supply source is configured to be selectively in fluid communication with the fluid port to supply a first fluid to the microwave ablation antenna assembly. The second fluid supply source is configured to be selectively in fluid communication with the fluid port to supply a second fluid to the microwave ablation antenna assembly.

In another aspect of the present disclosure, the first fluid supply source includes the first fluid, the second fluid supply source includes the second fluid, and the first fluid and the second fluid are different from each other.

In another aspect of the present disclosure, the first fluid is sterile water and the second fluid is saline.

In another aspect of the present disclosure, the system also includes a valve disposed between the first fluid supply source, the second fluid supply source, and the fluid port, wherein the valve is configured to be movable between a first position and a second position, the first position provides fluid communication between the first fluid supply source and the fluid port, and the second position provides fluid communication between the second fluid supply source and the fluid port.

In still another aspect of the present disclosure, the microwave ablation antenna assembly includes a probe having a tube, a feedline, and a fluid channel, the feedline extending through the tube and configured to be electrically coupled to the generator, and the fluid channel defined between the feedline and the tube and in fluid communication with the fluid port.

In another aspect of the present disclosure, the system further includes a pump disposed between the first fluid supply source, the second fluid supply source, and the microwave ablation antenna assembly, the pump configured to selectively receive fluid from the first fluid supply source or the second fluid supply source and to pump the first fluid or the second fluid to the microwave ablation antenna assembly.

In embodiments, the first and second fluid supply sources may be configured to be individually, detachably coupled to the microwave ablation antenna assembly. The first fluid supply source may be coupled to the microwave ablation antenna assembly when a first ablation zone size is desired, and the second fluid supply source may be coupled to the microwave ablation antenna assembly when a second ablation zone size is desired.

In still another aspect of the present disclosure, the system also includes a user interface on a display, a processor and a memory coupled to the display, the first fluid supply source, and the second fluid supply source. The user interface on the display is configured to receive a user input indicating a selection of the first fluid supply source or the second fluid supply source. The memory includes instructions which, when executed by the processor cause the system to, in response to the received user input, supply the first fluid from the first fluid supply source or the second fluid from the second fluid supply source to the microwave ablation antenna assembly.

In another aspect of the present disclosure, the display displays a first button and a second button, the first button indicating a first ablation zone size being associated with the first fluid supply source, and the second button indicating a second ablation zone size being associated with the second fluid supply source.

In still another aspect of the present disclosure, the memory includes instructions which, when executed by the processor cause the system to, in response to receiving an input to select the first button or the second button, display a representation indicating a name of a first fluid type corresponding to the first ablation zone size, or a representation indicating a name of a second fluid type corresponding to the second ablation zone size.

According to another aspect of the present disclosure, a method of operating a microwave ablation system is provided. The method includes selecting a first fluid supply source or a second fluid supply source. A first fluid is supplied from the first fluid supply source to a microwave ablation probe in response to the selection of the first fluid supply source and/or a second fluid from the second fluid supply source is supplied to the microwave ablation probe in response to the selection of the second fluid supply source.

Some methods may further include detecting a position of a valve configured to be movable between a first position and a second position. The first position permits the first fluid to be supplied to the microwave ablation probe, and the second position permits the second fluid to be supplied to the microwave ablation probe.

Some methods may further include receiving an input associated with the selection. The input may be received at a user interface. The user interface may be disposed on a display, and the method may further include displaying a first button associated with the first fluid supply source and a second button associated with the first fluid supply source.

Some methods may further include displaying a first button and a second button. The first button may be associated with a first ablation zone size and the second button may be associated with a second ablation zone size.

Some methods may further include in response to receiving an input to select the first button or the second button, displaying a representation indicating a name of a first fluid type corresponding to the first ablation zone size, or a representation indicating a name of a second fluid type corresponding to the second ablation zone size.

Some methods may further include performing one of pumping the first fluid supply source from the first fluid supply source to the microwave ablation probe, or pumping the second supply source from the second supply source to the microwave ablation probe.

In some aspects, the first fluid may be saline, and the second fluid may be sterile water.

In some aspects, selecting may include a manual coupling of the first fluid supply source or the second fluid supply source to the microwave ablation probe.

Any of the above aspects and embodiments of the present disclosure may be combined without departing from the scope of the present disclosure.

BRIEF DESCRIPTION OF THE DRAWINGS

Objects and features of the present disclosure will become apparent to those of ordinary skill in the art when descriptions of various embodiments thereof are read with reference to the accompanying drawings, of which.

DETAILED DESCRIPTION

Figure 1:
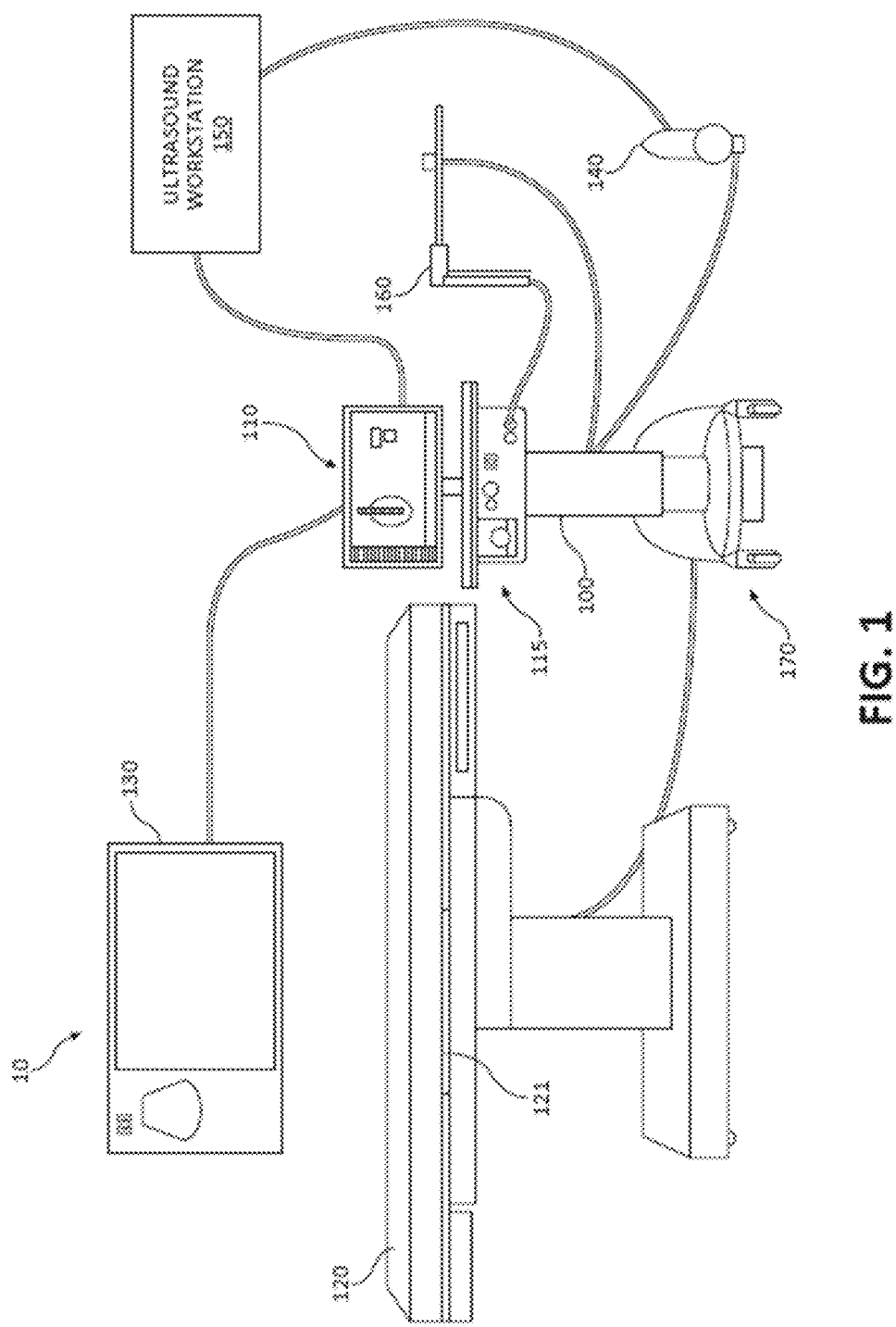
FIG. 1 is a side view of a microwave ablation system provided in accordance with the present disclosure.

A microwave ablation system is described herein that provides improved control of the size of an "ablation zone" resulting from passing electrosurgical energy through a probe of the system and into surrounding tissue and improved control of a maximum temperature resulting from the ablative energy emitted from the probe. In particular, the size of the ablation zone and/or the maximum temperature is selectable, based on a particular type of fluid that is circulated through the probe via a fluid circulation system included as part of the microwave ablation system. In this regard, the microwave ablation system is equipped with at least two fluid supply sources to provide different types of fluids to the probe. For example, one fluid supply source may contain saline, and the other fluid supply source may contain sterile water. A valve or other mechanism is included to permit selection of one of the fluid supply sources over the other. In this way, the ablation zone size, the maximum allowable temperature or both, may be controlled by the selection of a particular one of the fluids.

Although contemplated to be implemented in the liver or kidney, the embodiments described herein are not limited to application of any particular tissue or organ for treatment, indeed, it is contemplated that the systems and methods of the present disclosure may be used to treat pancreatic tissue, gastrointestinal tissue, interstitial masses, and other portions of the body known to those of skill in the art to be treatable via microwave ablation. These and other aspects of the present disclosure are described in greater detail below.

Hereinafter, embodiments of energy-delivery devices with a probe assembly and systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) (3×108 cycles/second) to 300 gigahertz (GHz) (3×1011 cycles/second). As it is used in this description, "ablation procedure" generally refers to any ablation procedure, such as, for example, microwave ablation, radiofrequency (RF) ablation, or microwave or RF ablation-assisted resection.

Referring now to FIG. 1, an exemplary microwave ablation system 10 of the present disclosure is depicted. The microwave ablation system 10 includes a computing device 100 storing one or more ablation planning and electromagnetic tracking applications, a touch display computer 110, microwave ablation generator 115, an operating table 120, including an electromagnetic (EM) field generator 121, a second display 130, an ultrasound imaging sensor 140, an ultrasound workstation 150, a microwave ablation antenna assembly 160, and a base unit 170 configured to support computing device 100, the microwave ablation generator 115, and the touch display computer 110. Computing devices described herein may be, for example, a laptop computer, desktop computer, tablet computer, or other similar device.

Touch display computer 110 is configured to control microwave generator 115, pump 117 (FIG. 2), microwave ablation antenna assembly 160, and other accessories and peripheral devices relating to, or forming part of, microwave ablation system 10. Touch display computer 110 is configured to present a user interface, for example, on a display, enabling a clinician to input instructions and settings for the microwave ablation generator 115, display images, and/or messages relating to the performance of the microwave ablation generator 115, the progress of a procedure, and issue alarms or alerts related to the same. Touch display computer 110 may display images or icons used for the selection of an ablation zone size, or for the selection of various parameters related to achieving an ablation zone size, such as power, duration, fluid type, and the like. The icons may be depicted graphically, numerically, symbols, words or other indicators. For example, the icons depicting the ablation zone sizes may include indication of "large" or "small" or numbers indicating the particular ablation zone sizes. Additional images or icons may depict an indication to alert the user of a potential of exceeding a maximum temperature threshold, and may include indication of "high" or "low" or numbers indicating particular temperatures or temperature ranges.

Operating table 120 may be any table suitable for use during a surgical procedure, which in certain embodiments includes or is associated with an EM field generator 121. EM field generator 121 is used to generate an EM field during the microwave ablation procedure and forms part of an EM tracking system, which is used to track the positions of surgical instruments, e.g., microwave ablation antenna assembly 160 and ultrasound sensor 140, within the EM field around and within the body of a patient. Second display 130, in association with computing device 100, may be used for displaying ultrasound imaging and providing visualization of tissue to be treated as well as navigation of the microwave ablation antenna assembly 160. However, it is envisioned that touch display computer 110 and computing device 100 may also be used for ultrasound imaging and navigation purposes in addition to its microwave ablation generator 115 control functions discussed above.

As will be described in more detail below (FIG. 2 and FIG. 3), microwave ablation antenna assembly 160 is used to ablate tissue, e.g., a target site, by using microwave energy to heat tissue in order to denature or kill cancerous cells. Further, although an exemplary microwave ablation antenna assembly 160 is detailed herein, it is contemplated that other suitable microwave ablation antennas may be utilized in accordance with the present disclosure. For example, the ablation antennas and systems described in U.S. Patent Application Publication No. 2016/0058507 entitled MICROWAVE ABLATION SYSTEM, filed on Aug. 18, 2015 by Dickhans, International Application No. PCT/US15/46729 entitled MICROWAVE ABLATION SYSTEM, filed on Aug. 25, 2015 by Dickhans, U.S. Pat. No. 9,247,992 entitled MICROWAVE ABLATION CATHETER AND METHOD OF UTILIZING THE SAME, issued on Feb. 2, 2016 by Ladtkow et al., U.S. Pat. No. 9,119,650 entitled MICROWAVE ENERGY-DELIVERY DEVICE AND SYSTEM, issued on Sep. 1, 2015 by Brannan et al., the entire contents of each of which are incorporated herein by reference, may be used in conjunction with the aspects and features of the present disclosure.

In addition to the EM tracking system, the surgical instruments, e.g., microwave ablation antenna assembly 160, may also be visualized by using ultrasound imaging work station 150. Ultrasound sensor 140, which may be, e.g., an ultrasound wand, may be used to image the patient's body during the microwave ablation procedure to visualize the location of microwave ablation antenna assembly 160 inside the patient's body. Ultrasound sensor 140 may have an EM tracking sensor embedded within or attached to the ultrasound wand, for example, a clip-on sensor or a sticker sensor. Ultrasound sensor 140 may be positioned in relation to microwave ablation antenna assembly 160 such that microwave ablation antenna assembly 160 is at an angle to the ultrasound image plane, thereby enabling the clinician to visualize the spatial relationship of microwave ablation antenna assembly 160 with the ultrasound image plane and with objects being imaged. Further, the EM tracking system may also track the location of ultrasound sensor 140. This spatial depiction of the ultrasound sensor 140 and the microwave ablation antenna assembly 160 is described in greater detail in U.S. Patent Application No. 62/154,924 entitled METHODS FOR MICROWAVE ABLATION PLANNING AND PROCEDURE, filed on Apr. 30, 2015 by Girotto, which is incorporated herein by reference. During surgery, one or more ultrasound sensors 140 may be placed on or inside the body of the patient. EM tracking system may then track the location of such ultrasound sensors 140 and microwave ablation antenna assembly 160 as they are moved relative to each other. It is also envisioned that ultrasound workstation 150 and its related components may be interchanged with real time fluoroscopy, MRI or CT imaging stations.

Figure 2:
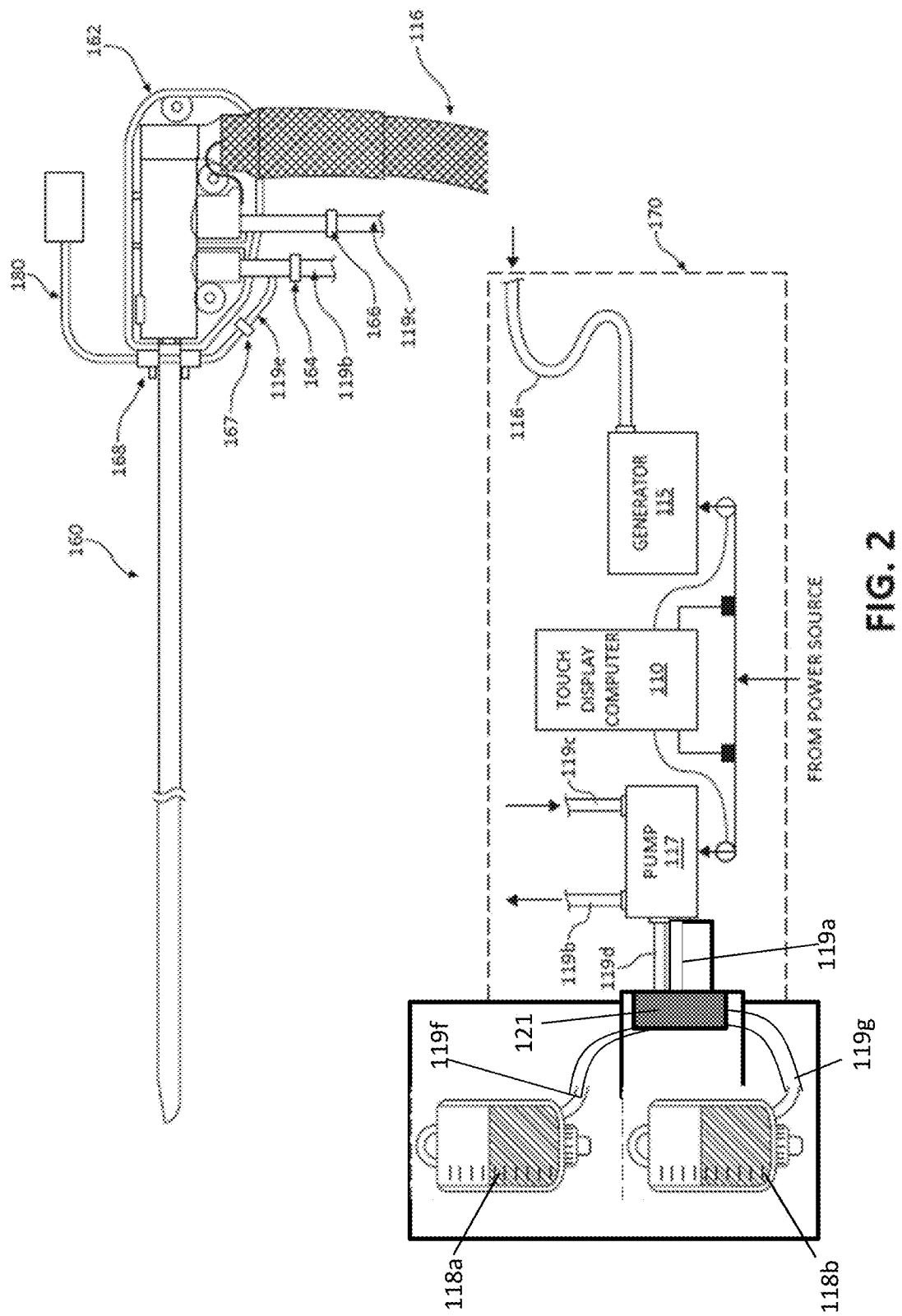
FIG. 2 is a side, partial cross-sectional view of a microwave ablation antenna assembly and base unit.

With additional reference to FIG. 2, microwave ablation antenna assembly 160, microwave ablation generator 115, touch display computer 110, and pump 117 are depicted schematically as housed on base unit 170 of system 10 (FIG. 1). Microwave ablation antenna assembly 160 is coupled to a microwave generator 115 via a flexible coaxial cable 116. Microwave generator 115 is configured to provide microwave energy at an operational frequency from about 915 MHz to about 2.45 GHz, although other suitable frequencies are also contemplated. Microwave ablation antenna assembly 160 may include a connection hub 162 for connection of coaxial cable 116, as well as the connection of a fluid inlet port 164 and a fluid outlet port 166. Fluid inlet port 164 permits the ingress of fluid into the microwave ablation antenna assembly 160 for circulating fluid around components housed therein and controlling the energy dissipation of microwave energy. Fluid outlet port 166 permits the egress of the fluid following circulation of the fluid through the microwave ablation antenna assembly 160.

The ports 164 and 166 are also coupled to pump 117 that is, in turn, coupled to multiple supply sources 118a, 118b (two of which are shown here) via a connection lines 119a, 119f, 119g. In embodiments, only one supply source 118a may be provided. Each supply source 118 may be a fluid filled bag, as depicted in FIG. 2, or any other type of storage unit for any type of fluid such as a tank, reservoir or other container. Pump 117 may be a positive displacement pump, such as a peristaltic pump. Each supply source 118a, 118b stores a fluid and may maintain the fluid at a predetermined temperature. In an embodiment, the supply sources 118a, 118b each include a fluid that when circulated through the microwave ablation assembly 160 during an ablation procedure causes the microwave ablation assembly 160 to generate an ablation zone having a predetermined size or provides improved control of a maximum temperature output.

To generate ablation zones having different sizes, different fluids may be included in each supply source 118a, 118b. According to an embodiment, one of the supply sources 118a, 118b stores sterile water, while the other of the supply sources 118a, 118b stores saline. In another embodiment, one or both of the supply sources 118a, 118b stores a biocompatible fluid other than water. Further, in another embodiment, the fluid may be in the form of a gas and/or a mixture of liquid and gas. In embodiments, both of the supply sources 118a, 118b may store sterile water. It will be appreciated that as the fluid (e.g., sterile water) circulates in and around the microwave ablation antenna assembly 160, the presence of the fluid harmonizes the susceptance, and hence impedance, of the tissue through which the microwave energy is passing. More particularly, by employing water as the circulating fluid, the same impedance is provided for the entirety of the area receiving the microwave energy, thereby minimizing potential energy losses in the microwave ablation antenna assembly 160 and providing a more definable and modeled reaction to the microwave energy. In this way, the improved heat absorption by the tissue yields a well-defined ablation, to provide a better, more controlled treatment result.

In an embodiment, the supply sources 118a, 118b are each connected to a valve 121 by connection lines 119f, 119g, respectively. The valve 121 may be electrically activated or coupled to a mechanism accessible to the user to be manually activated. For example, the valve 121 may be movable between various positions, where when in one position, fluid communication is provided between the connection line 119a and supply source 118a, while when in another position, fluid communication is provided between the connection line 119a and supply source 118b. In any case, by positioning the valve 121 between the supply sources 118a, 118b, and the connection line 119a, the user is permitted to select which ones of the supply sources 118a, 118b will supply fluid to the microwave ablation assembly 160.

In addition to providing improved harmonization of impedance of the tissue during the ablation procedure, the fluid may be used as a coolant. In an embodiment, the supply sources 118a, 118b may include coolant units (not explicitly shown) that cool returning liquid from the microwave ablation antenna assembly 160. Pump 117 forces fluid from supply source 118 through a supply line 119b into microwave ablation antenna assembly 160, such that heat is drawn away from the microwave ablation antenna assembly 160, which may enhance the overall ablation pattern, prevent damage to microwave ablation antenna assembly 160, and prevent harm to the clinician or patient. The fluid is returned to pump 117 and, ultimately, supply source 118a, 118b, via return line 119c and pump return line 119d. Connected to and branching from supply line 119b is an irrigation line 119e, which includes a valve 167 and an outlet nozzle 168.

Figure 3:
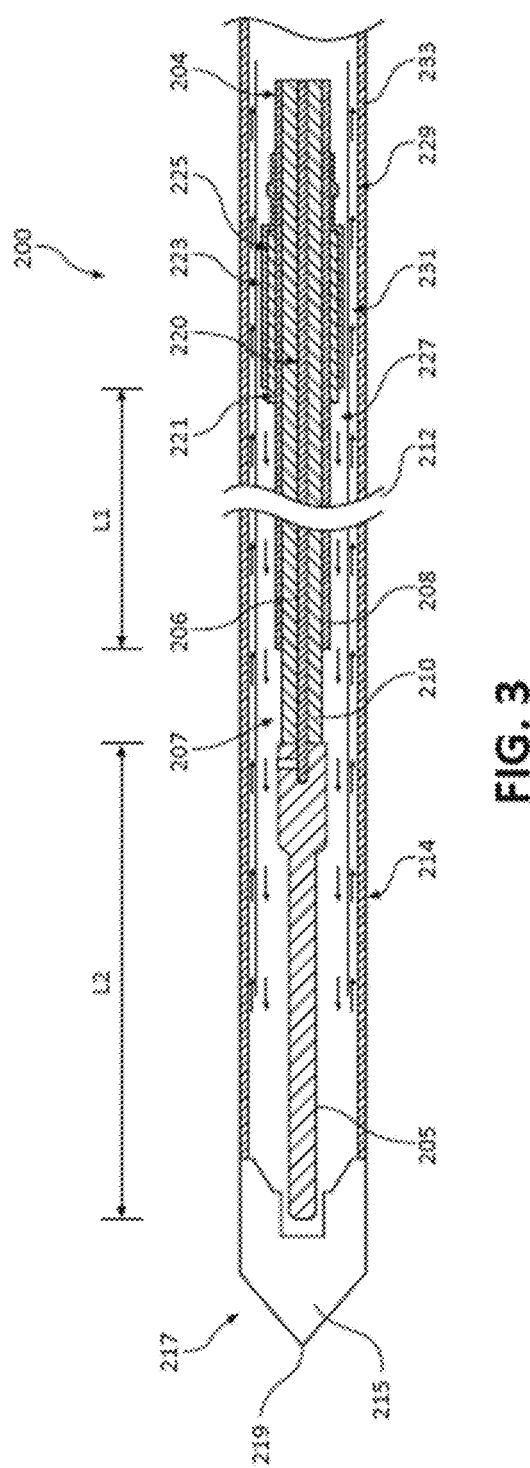
FIG. 3 is a cross-sectional view of a distal end of the antenna assembly of FIG. 2.

FIG. 3 illustrates the distal portion 200 of the microwave ablation antenna assembly 160. Distal portion 200 of microwave ablation antenna assembly 160 includes a proximal radiating portion 212 having a length "L1," and a distal radiating portion 214 having a length "L2," including an electrically-conductive radiator 205 and a feed point 207 disposed between the proximal and distal radiating portions 212 and 214, respectively. A feedline 204 is formed of a coaxial cable having an inner conductor 206, and outer conductor 208, and a dielectric 210 separating the two. The feedline 204 is connected at its proximal end to flexible cable 116 (FIG. 2). The distal radiating portion 214 and the proximal radiating portion 212 may be either balanced (e.g., of equal lengths) or unbalanced (e.g., of unequal lengths). The proximal radiating portion 212 may be formed of a portion of the feedline 204.

The microwave ablation antenna assembly 160 also includes a balun (e.g., a choke) 220 disposed around the feedline 204. The balun 220 may be a quarter-wavelength balun formed of at least a dielectric layer 221 and a conductive layer 223. The conductive layer 223 may be shorted to the feedline 204 at the proximal end of the balun 220 by soldering or other suitable methods, or may be in electrical contact with a balun short 225 which itself is in electrical contact with the outer conductor 208 of the feedline 204. Microwave ablation antenna assembly 160 also includes a tip 215 having a tapered end 217 that terminates, in one embodiment, at a pointed end 219 to allow for insertion into tissue with minimal resistance. In cases where the microwave ablation assembly 160 is inserted into a pre-existing opening, tip 215 may be rounded or flat. The tip 215 may be formed from a variety of heat-resistant materials suitable for penetrating tissue, such as metals (e.g., stainless steel) and various thermoplastic materials, such as polyetherimide, and polyamide thermoplastic resins.

The microwave ablation antenna assembly 160 includes fluid channels 227 and 229. Fluid channel 227 is spaced between the feedline 204 (including its electrically connected components balun 220 and proximal and distal radiating portions 212 and 214) and an inner tube 231. Fluid channel 229 is formed between the inner tube 231 and an outer cannula 233 of the microwave ablation antenna assembly 160. Fluid channel 227 connects to fluid inlet port 164 and fluid channel 229 connects to fluid outlet port 166, thereby completing a fluid circuit from the fluid tanks 118a, 118b, through the pump 117, and through the microwave ablation antenna assembly 160.

To operate the microwave ablation system 10, at some point prior to performing the ablation procedure, the system 10 is powered on. Once the system 10 is powered on, the touch display computer 110 may display various icons and/or information relating to parameters that may be selected by the user or presented to the user for consideration. For example, the touch display computer 110 may display icons indicating ablation zone sizes, for example, "large" or "small", numerical sizes and the like. In another embodiment, in addition or as an alternative to simply selecting ablation zone size, other images may be displayed, for example selectable icons or explanatory text indicating parameters corresponding to the power to be provided by microwave ablation generator 115, duration of ablation, and/or fluid type required to permit microwave ablation system 10 to output a particular ablation zone size.

It will be appreciated that the desired ablation zone size to be employed during the ablation procedure on target tissue is typically identified based on previously analysis of obtained images of the tissue during a planning phase. In accordance with an embodiment, the selections are received at the touch display computer 110, for example, by the user tapping on the appropriate icon. In another embodiment, the user may consider the explanatory text corresponding to an ablation zone size and may input the selection at the valve 121. In any case, in response to receiving the selection, the system 10 causes the valve 121 to be actuated, the user actuates the valve 121 or the valve 121 is otherwise placed in a position to permit fluid communication between the selected supply source 118a or 118b and the connection line 119a. The generator 115 draws power from a power source and provides the power to the microwave ablation antenna assembly 160 via the cable 116, and the pump 117 is powered via the power source and begins to receive fluid from the selected supply source 118a, 118b, through the supply line 119b into microwave ablation antenna assembly 160. The fluid is circulated into fluid channel 227 via fluid inlet port 164 and through fluid channel 229 out to fluid outlet port 166, and in a configuration in which a coolant unit is included, to thereby draw heat away from the microwave ablation antenna assembly 160.

Figure 5:
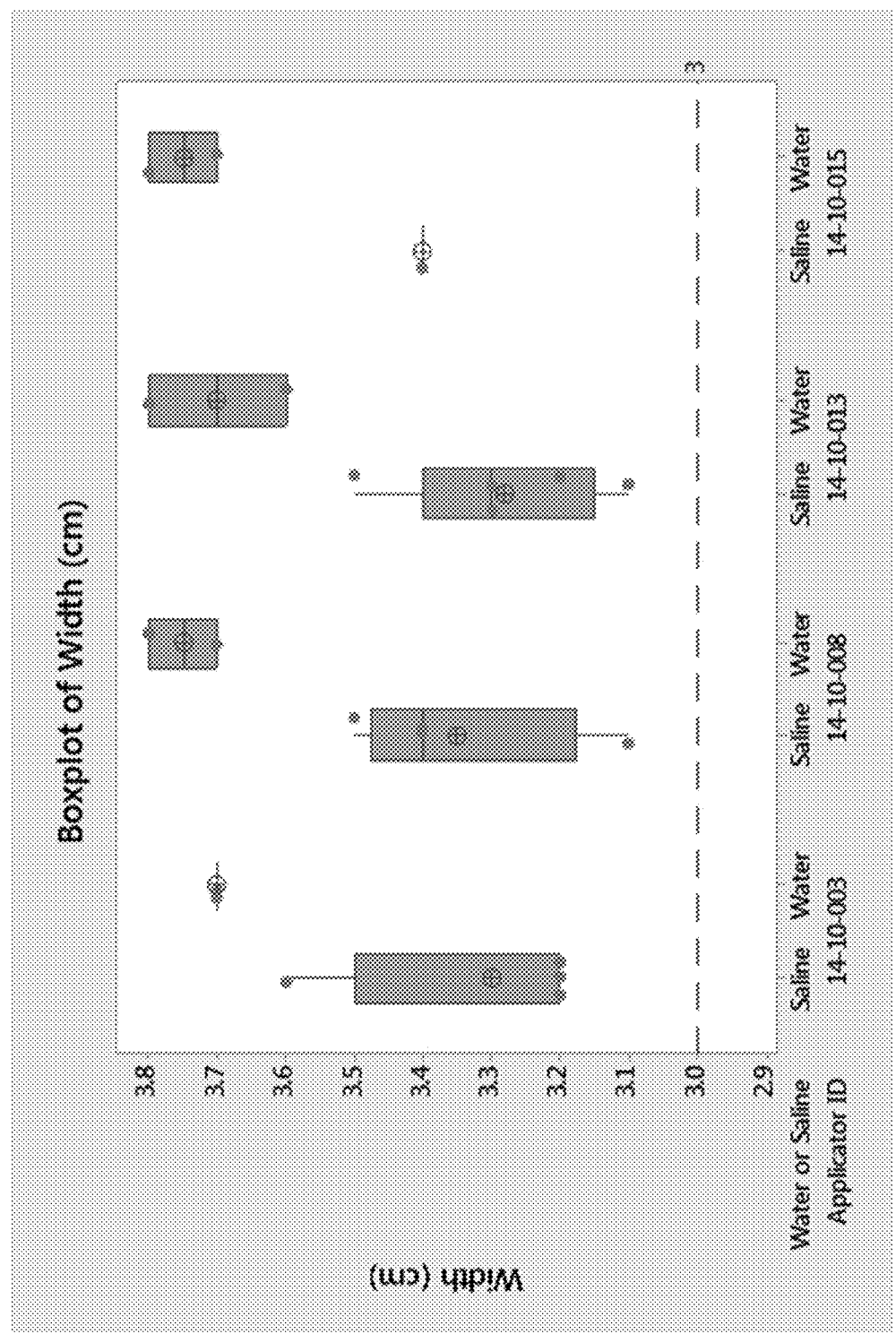
FIG. 5 is a graph illustrating the diameters of the ablation zone using saline versus sterile water as the dielectric.
Figure 6:
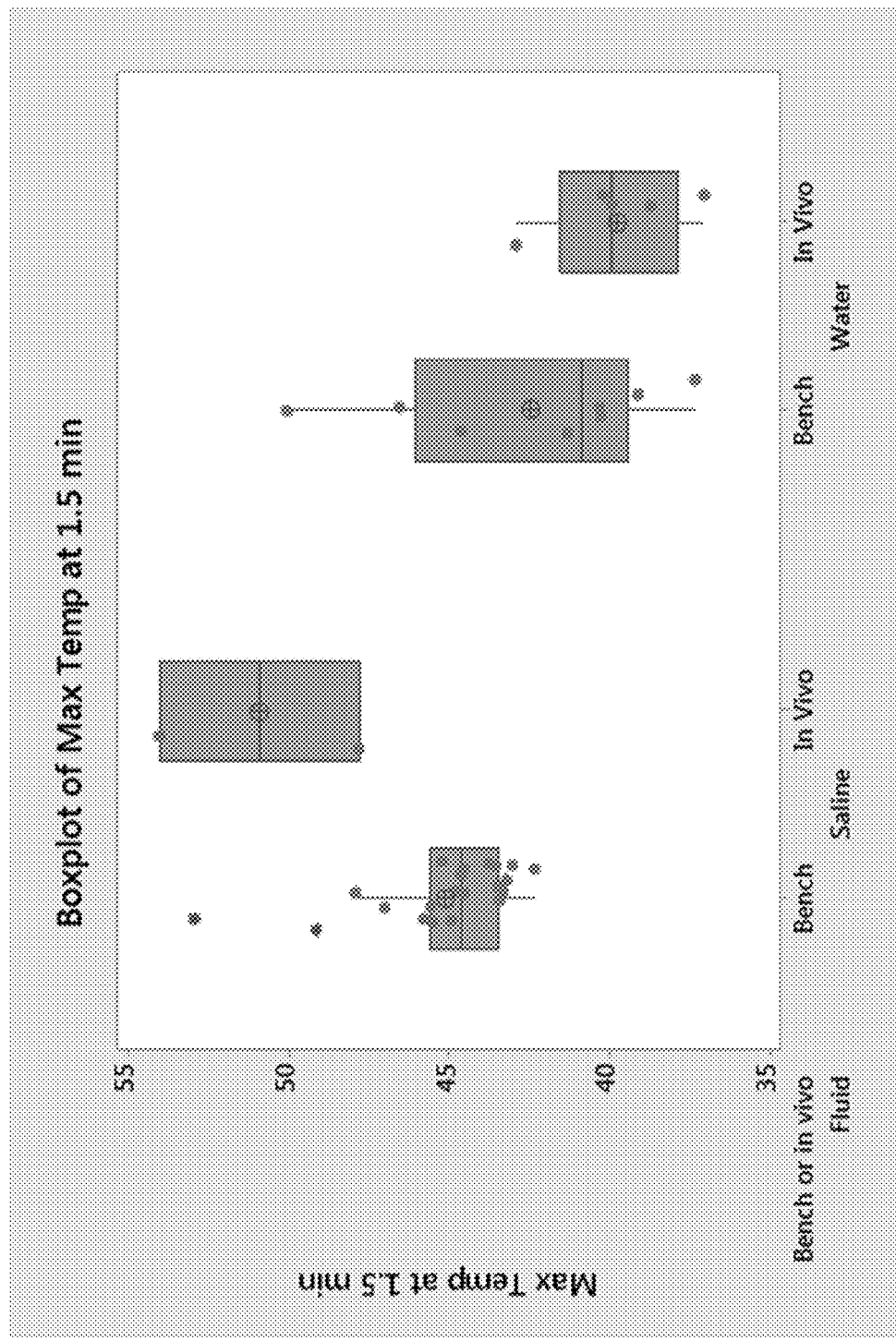
FIG. 6 is a graph illustrating the maximum temperatures from the ablative energy of the microwave ablation antenna assembly at 1.5 minutes.

In an embodiment in which saline is used as one of the supply sources 118a, 118b, the diameter of the ablation zone is typically in a range of about 3.0 mm to about 3.6 mm. In another embodiment, the diameter of the ablation zone when saline is used is in a range of about 3.2 mm to about 3.6 mm. In still another embodiment, the ablation zone diameter when saline is used is in a range of about 3.1 mm to about 3.5 mm. In embodiments, the average ablation size using sterile saline is about 3.35 cm, as shown in Table 1. According to an embodiment, as detailed below, unexpectedly, when the fluid is changed to another type, the diameter of the ablation zone can be changed as well. For example, as illustrated in FIG. 5, in an embodiment in which sterile water is used as the supply source 118a, 118b, the diameter of the ablation zone is larger than when saline is used and typically has a diameter in a range of about 3.6 mm to about 3.8 mm. As also illustrated in FIG. 5, in another embodiment in which sterile water is employed, the diameter of the ablation zone is in a range of about 3.7 mm to about 3.8 mm. In embodiments, the average ablation size using sterile water is about 3.75 cm, as shown in Table 1.

Figure 4:
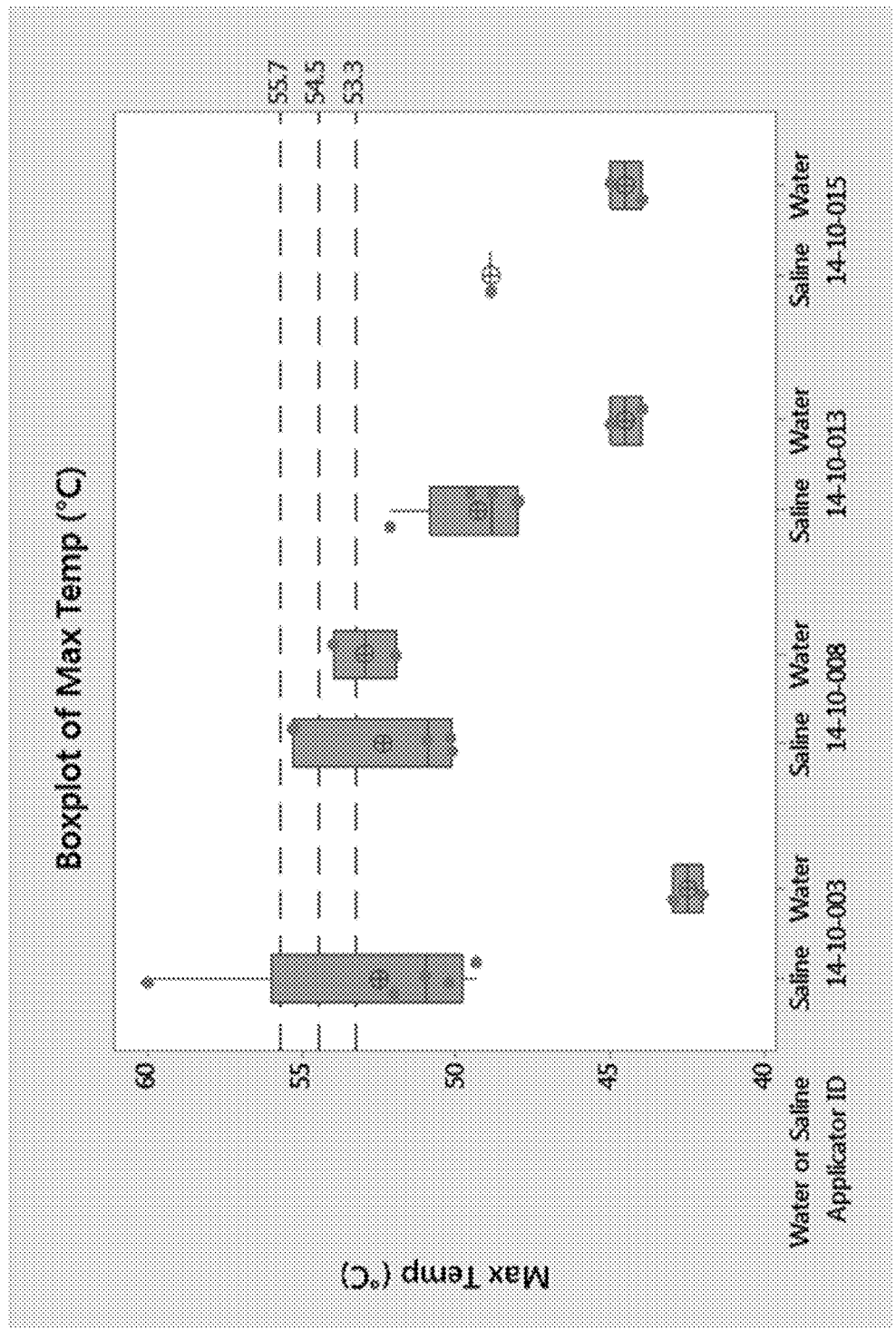
FIG. 4 is a graph illustrating the maximum temperatures from the ablative energy of the microwave ablation antenna assembly using saline versus sterile water as the dielectric.

Furthermore, unexpectedly, when saline is used as one of the supply source 118a, 118b, the maximum temperature from the ablative energy of the microwave ablation antenna assembly 160 is in a range of about 40° C. to about 70° C., or in some embodiments, about 51° C., as shown in Table 1. With reference to FIG. 4, according to another embodiment in which sterile water is used as the supply sources 118a, 118b, the maximum temperature output from the ablative energy of the microwave ablation antenna assembly 160 is less than when saline is used. In an embodiment, when sterile water is used as one of the supply source 118a, 118b, the maximum temperature from the ablative energy of the microwave ablation antenna assembly 160 is in a range of about 30° C. to about 60° C., or in some embodiments, about 46.5° C.

TABLE 1

Average Maximum Temperature and Average Ablation Size for Sterile Water and Sterile Saline

| Fluid Type | Average Max Temp | Average Ablation Size |
|---|---|---|
| Sterile Water | 46.5 C. | 3.75 cm |
| Sterile Saline | 51 C. | 3.35 cm |

Figure 7:
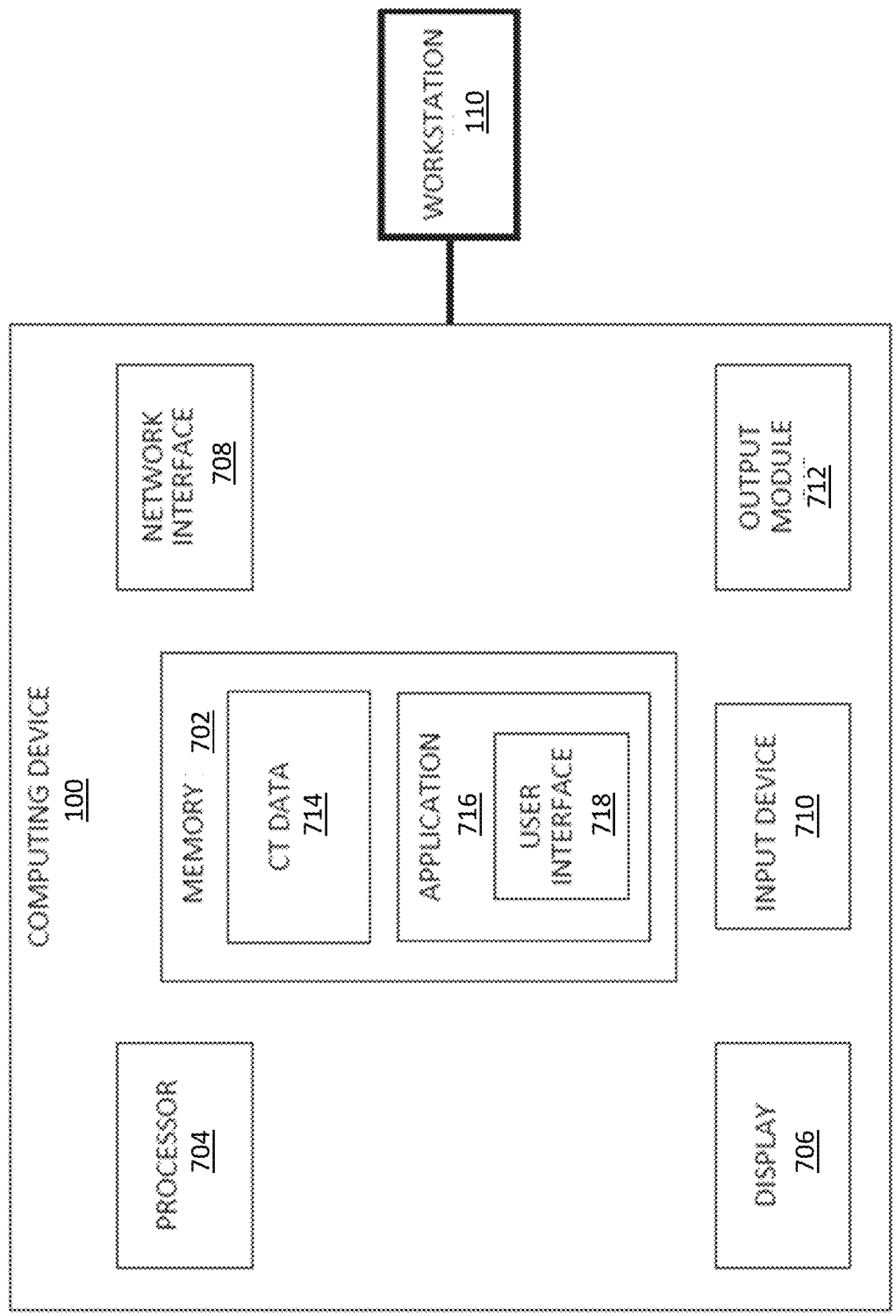
FIG. 7 is a block diagram of a computing device that may be implemented as part of the microwave ablation system, in accordance with an embodiment of the present disclosure.

As noted above, the microwave ablation system 10 implements a computing device 100. In an embodiment, as shown in FIG. 7, the computing device 100 may include a memory 702, a processor 704, display 706, a network interface 708, an input device 710, and/or an output module 712.

The memory 702 includes any non-transitory computer-readable storage media for storing data and/or software that is executable by the processor 704 and which controls the operation of the computer 110. In an embodiment, the memory 702 may include one or more solid-state storage devices such as flash memory chips. Alternatively, or in addition to the one or more solid-state storage devices, the memory 702 may include one or more mass storage devices connected to the processor 704 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 704. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the workstation 150.

The memory 702 may store an application 716. The application 716 may, when executed by the processor 704, cause the display 706 to present the user interface 718. The network interface 708 may be configured to connect to a network such as a local area network (LAN) consisting of a wired network and/or a wireless network, a wide area network (WAN), a wireless mobile network, a Bluetooth network, and/or the internet. The input device 710 may be any device by means of which a user may interact with the computer 110, such as, the touch screen of the touch screen computer 110 or may include another device coupled thereto, for example, a mouse, keyboard, foot pedal, and/or voice interface. The output module 712 may include any connectivity port or bus, such as, for example, parallel ports, serial ports, universal serial busses (USB), or any other similar connectivity port known to those skilled in the art.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or submultiple of the wavelength of an electromagnetic wave or electrical signal propagating within a transmission medium. The wavelength may be expressed in radians or in artificial units of angular measure, such as degrees. The electrical length is in general different from the physical length. By the addition of an appropriate reactive element (capacitive or inductive), the electrical length may be made significantly shorter or longer than the physical length.

Various embodiments of the presently disclosed energy-delivery device with a fluid-cooled probe assembly including a balun are suitable for microwave or RF ablation and for use to pre-coagulate tissue for microwave or RF ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, the teachings of the present disclosure may apply to a monopole, dipole, helical, or other suitable type of microwave antenna or RF electrode.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave ablation system comprising:
a microwave ablation antenna assembly including a fluid port for receiving fluid;
a generator coupled to the microwave ablation antenna assembly;
a first fluid supply source configured to be selectively in fluid communication with the fluid port to supply a first fluid to the microwave ablation antenna assembly;
a second fluid supply source configured to be selectively in fluid communication with the fluid port to supply a second fluid to the microwave ablation antenna assembly;
a processor; and
a memory including instructions which, when executed by the processor cause the system to, in response to a user selecting the first fluid supply source or the second fluid supply source, supply the first fluid from the first fluid supply source or the second fluid from the second fluid supply source to the microwave ablation antenna assembly, and display a first button and a second button, the first button indicating a first ablation zone size associated with the first fluid supply source, and the second button indicating a second ablation zone size associated with the second fluid supply source.

2. The microwave ablation system of claim 1, wherein the first fluid supply source includes the first fluid, the second fluid supply source includes the second fluid, and the first fluid and the second fluid are different from each other.

3. The microwave ablation system of claim 2, wherein the first fluid is sterile water and the second fluid is saline.

4. The microwave ablation system of claim 1, further comprising a valve disposed between the first fluid supply source, the second fluid supply source, and the fluid port, wherein:
the valve is configured to be movable between a first position and a second position,
the first position provides fluid communication between the first fluid supply source and the fluid port, and
the second position provides fluid communication between the second fluid supply source and the fluid port.

5. The microwave ablation system of claim 4, wherein the microwave ablation antenna assembly includes a probe having a tube, a feedline, and a fluid channel, the feedline extending through the tube and configured to be electrically coupled to the generator, and the fluid channel defined between the feedline and the tube and in fluid communication with the fluid port.

6. The microwave ablation system of claim 1, further comprising a pump disposed between the first fluid supply source, the second fluid supply source, and the microwave ablation antenna assembly, the pump configured to selectively receive fluid from the first fluid supply source or the second fluid supply source to pump the first fluid or the second fluid to the microwave ablation antenna assembly.

7. The microwave ablation system of claim 1, wherein the first and second fluid supply sources are configured to be individually, detachably coupled to the microwave ablation antenna assembly, such that the first fluid supply source is coupled to the microwave ablation antenna assembly when the first ablation zone size is desired, and the second fluid supply source is coupled to the microwave ablation antenna assembly when the second ablation zone size is desired.

8. The microwave ablation system of claim 1, further comprising a display including a user interface, wherein the user interface on the display is configured to receive a user input indicating the selection of the first fluid supply source or the second fluid supply source.

9. The microwave ablation system of claim 1, wherein the memory includes instructions which, when executed by the processor cause the system to, in response to receiving an input to select the first button or the second button, display a representation indicating a name of a first fluid type corresponding to the first ablation zone size, or a representation indicating a name of a second fluid type corresponding to the second ablation zone size.

10. A method of operating a microwave ablation system, the method comprising:
selecting between a first ablation zone size and a second ablation zone size; and
supplying either a first fluid or a second fluid to a microwave ablation probe based on whether the first ablation zone size or the second ablation zone size is selected.

11. The method of claim 10, further comprising detecting a position of a valve configured to be movable between a first position and a second position, wherein the first position permits the first fluid to be supplied to the microwave ablation probe, and the second position permits the second fluid to be supplied to the microwave ablation probe.

12. The method of claim 10, further comprising receiving an input associated with the selection, wherein the input is received at a user interface.

13. The method of claim 12, wherein the user interface is disposed on a display, and the method further comprises displaying a first button associated with a first fluid supply source and a second button associated with a first fluid supply source.

14. The method of claim 13, wherein the first button is associated with the first ablation zone size and the second button is associated with the second ablation zone size.

15. The method of claim 14, further comprising in response to receiving an input to select the first button or the second button, displaying a representation indicating a name of a first fluid type corresponding to the first ablation zone size, or a representation indicating a name of a second fluid type corresponding to the second ablation zone size.

16. The method of claim 10, further comprising performing one of pumping the first fluid from a first fluid supply source to the microwave ablation probe, or pumping the second fluid from a second supply source to the microwave ablation probe.

17. The method of claim 10, wherein the first fluid is saline, and the second fluid is sterile water.

18. The method of claim 10, wherein selecting includes a manual coupling of a first fluid supply source or a second fluid supply source to the microwave ablation probe.

* * * * *